(12) United States Patent
Corroy et al.

(10) Patent No.: US 8,535,223 B2
(45) Date of Patent: Sep. 17, 2013

(54) WIRELESS PATIENT MONITORING USING STREAMING OF MEDICAL DATA WITH BODY-COUPLED COMMUNICATION

(75) Inventors: Steven Corroy, Aachen (DE); Karin Klabunde, Bochum (DE); Heribert Baldus, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 363 days.

(21) Appl. No.: 12/918,840

(22) PCT Filed: Feb. 19, 2009

(86) PCT No.: PCT/IB2009/050674
§ 371 (c)(1),
(2), (4) Date: Aug. 23, 2010

(87) PCT Pub. No.: WO2009/107040
PCT Pub. Date: Sep. 3, 2009

(65) Prior Publication Data
US 2011/0004073 A1    Jan. 6, 2011

(30) Foreign Application Priority Data
Feb. 28, 2008   (EP) ................... 08102098

(51) Int. Cl.
*A61B 5/00*   (2006.01)

(52) U.S. Cl.
USPC ........... 600/300; 600/301; 455/41.1; 375/343

(58) Field of Classification Search
USPC ....... 600/300–301, 534; 340/539.12–539.14, 340/286.1; 705/2–5; 343/718; 455/41.1; 375/343
See application file for complete search history.

(56) References Cited

U.S. PATENT DOCUMENTS

| | | | |
|---|---|---|---|
| RE32,180 E * | 6/1986 | Lewiner et al. | 340/573.1 |
| 4,971,065 A * | 11/1990 | Pearce | 600/534 |
| 6,211,799 B1 | 4/2001 | Post et al. | |
| 6,942,624 B2 * | 9/2005 | Takizawa et al. | 600/534 |
| 7,011,814 B2 * | 3/2006 | Suddarth et al. | 424/9.2 |
| 7,406,349 B2 | 7/2008 | Seeberger et al. | |
| 7,436,311 B2 * | 10/2008 | Rapaport et al. | 340/573.1 |
| 7,538,667 B2 * | 5/2009 | Koen | 340/539.13 |
| 8,095,381 B2 * | 1/2012 | Simons et al. | 705/2 |
| 8,269,634 B2 * | 9/2012 | Fischell et al. | 340/573.1 |
| 2003/0136201 A1 * | 7/2003 | Hubbard, Jr. | 73/862.41 |
| 2004/0082874 A1 * | 4/2004 | Aoki et al. | 600/534 |
| 2005/0177051 A1 * | 8/2005 | Almen | 600/509 |
| 2006/0031378 A1 | 2/2006 | Vallapureddy et al. | |

(Continued)

FOREIGN PATENT DOCUMENTS

| | | |
|---|---|---|
| EP | 1168678 A1 | 1/2002 |
| JP | 2005137813 A | 6/2005 |

(Continued)

*Primary Examiner* — Bill Thomson
*Assistant Examiner* — Bobby Soriano

(57) ABSTRACT

The invention relates to a system and method for wirelessly monitoring a patient (4), the system comprising a medical sensor (1) for collecting medical data and a coupling interface (2) for coupling with a monitor (3). The medical sensor (1) is attached to the patient's (4) body, and the medical data collected by the medical sensor (1) is transmitted to the coupling interface (2) via body-coupled communication (5). Preferably, the collected medical data is streamed to the coupling interface (2) via body-coupled communication (5). This way, a secure and reliable system and method for wireless patient monitoring are achieved which only require little power.

15 Claims, 4 Drawing Sheets

(56) References Cited

U.S. PATENT DOCUMENTS

| | | | |
|---|---|---|---|
| 2006/0208880 A1* | 9/2006 | Funk et al. | 340/539.26 |
| 2006/0224048 A1* | 10/2006 | Devaul et al. | 600/300 |
| 2007/0049842 A1* | 3/2007 | Hill et al. | 600/534 |
| 2007/0055166 A1* | 3/2007 | Patil | 600/509 |
| 2007/0130657 A1* | 6/2007 | Rogers et al. | D24/107 |
| 2007/0135866 A1* | 6/2007 | Baker et al. | 607/60 |
| 2008/0004904 A1* | 1/2008 | Tran | 705/2 |
| 2008/0094256 A1* | 4/2008 | Koen | 340/988 |
| 2008/0186241 A1* | 8/2008 | Christensen | 343/718 |
| 2008/0294019 A1* | 11/2008 | Tran | 600/301 |
| 2009/0118596 A1* | 5/2009 | Khanuja et al. | 600/301 |
| 2009/0203973 A1* | 8/2009 | Donoghue et al. | 600/301 |
| 2009/0318779 A1* | 12/2009 | Tran | 600/301 |
| 2010/0121157 A1* | 5/2010 | Espina et al. | 600/301 |
| 2010/0168530 A1* | 7/2010 | Chetham et al. | 600/301 |
| 2010/0286490 A1* | 11/2010 | Koverzin | 600/301 |
| 2011/0054264 A1* | 3/2011 | Fischell et al. | 600/300 |
| 2012/0095299 A1* | 4/2012 | Sun et al. | 600/300 |
| 2012/0149996 A1* | 6/2012 | Stivoric et al. | 600/301 |
| 2012/0157795 A1* | 6/2012 | Chiu et al. | 600/301 |
| 2012/0310971 A1* | 12/2012 | Tran | 707/769 |

FOREIGN PATENT DOCUMENTS

| | | |
|---|---|---|
| WO | 2006064397 A2 | 6/2006 |
| WO | 2007028035 A2 | 3/2007 |
| WO | 2007096810 A1 | 8/2007 |

* cited by examiner

WIRELESS PATIENT MONITORING USING STREAMING OF MEDICAL DATA WITH BODY-COUPLED COMMUNICATION

FIELD OF THE INVENTION

The invention relates to the field of wireless patient monitoring and especially to ultra low power wireless patient monitoring with a medical sensor attached to a patient's body.

BACKGROUND OF THE INVENTION

Wireless sensor networks (WSNs) have been massively used for medical applications like patient monitoring where vital signs (e.g. electrocardiogram (ECG), photoplethysmograph (PPG), pulse oximetry (Sp02) or electroencephalography (EEG)) can be measured and transmitted by small sensor node platforms to a monitor for visualisation. These nodes form a network communicating via RF transmission and using protocols like e.g. IEEE 802.11, IEEE 802.15.4/Zigbee or Bluetooth. All of these radio standards consume a lot of energy and cannot be used for applications requiring very long life time because sensor nodes platforms are using batteries with few capacities.

Body-coupled communication (BCC) is a communication technology consisting in propagating an electric field on the human body in order to transmit information between two or more devices attached to the human body. Capacitive coupling to transmit data and power through a person's body is described in U.S. Pat. No. 6,211,799.

In general, for such a system using BCC, the transmitter and the receiver each have two conductive plates, i.e. one on the body and one in the air, which are used for propagating the electric field and which form an electric circuit composed by the human body and by a return path, i.e. air and ground. Such systems can be operated at different frequencies and are capable to achieve a data rate of few kbps.

SUMMARY OF THE INVENTION

It is the object of the invention to provide a system and method for wirelessly monitoring a patient which are secure and reliable and which only require little power.

This object is achieved by a system for wirelessly monitoring a patient, the system comprising
a medical sensor for collecting medical data and
a coupling interface for coupling with a monitor, wherein
the medical sensor is attached to the patient's body, and
the medical data collected by the medical sensor is transmitted to the coupling interface via body-coupled communication.

Accordingly, it is an important idea of the invention to restrict the communication between the medical sensor and the coupling interface to body-coupled communication. This has several advantages compared with the prior art that uses RF communication of the medical sensor with a receiver or a remote station like a monitor.

RF systems consume at least ten times more energy than the system according to the invention. In general, WSN nodes are equipped with low capacity batteries and have to last a very long period of time, typically months. Using the system according to the invention instead of a RF system multiplies sensor nodes life time by at least ten. Further, RF systems generally work at 2.4 GHz. This frequency is strongly attenuated by the human body and the quality of the transmitted signal is severely degraded.

Moreover the number of existing RF systems working at this frequency increases exponentially (e.g. IEEE 802.11, IEEE 802.15.4/Zigbee or Bluetooth) and the high level of interference on this frequency band strongly contributes to decrease the quality of communication whereas medical applications require an optimal data delivery ratio. From another perspective, introducing a new system working at 2.4 GHz would decrease the performance of all other existing systems also working at this frequency and thus disturb the current network architecture of e.g. an hospital.

The communication transport layer of RF standards like Zigbee or Bluetooth has the role to provide maximal data rate to one node depending on the condition of the network and at the same time to provide an equal data rate to all nodes in the network. In contrast to the invention, this leads to a waste of bandwidth, i.e. of energy, when the channel is empty because a node transmits at a higher data rate than its sample rate, and to a loss of information when the channel is completely full because data does not arrive in time any more since a lower data rate must be used.

Furthermore, medical data is very sensitive with respect to security. Generally, RF systems have a very large propagation range which enables eavesdropping of the transmitted data by a malicious node in this range. On the contrary, according to the invention, information transmitted by a system as described above stays on the human body making it much harder to intercept, requiring for the spy to touch the patient equipped with the monitoring system according to the invention in order to eavesdrop medical data.

Finally, in order to display medical data on a monitor, RF systems have to be associated to one specific monitor when there are many monitors in range. Moreover, many nodes may want to display information on the same screen. Therefore, RF systems use complex network protocols to solve these problems and enable a reliable peer-to-peer connection between a sensor node and a display monitor. On the contrary, with respect to the short propagation range of the system according to the invention, there could hardly be more than one monitor touched by the user and therefore the communication protocol stack of this system is simpler and more efficient.

According to a preferred embodiment of the invention, the medical sensor is adapted for one of the following measurements: electrocardiogram (ECG), photoplethysmograph (PPG), pulse oximetry (Sp02) or electroencephalography (EEG).

Generally, the system according to the invention can be provided with only one single medical sensor. However, according to a preferred embodiment of the invention, multiple medical sensors are provided on the patient's body. Further, according to a preferred embodiment of the invention, the medical data collected by multiple medical sensors is transmitted to the same coupling interface via body-coupled communication, and the coupling interface acts as a gateway for collecting the medical data from the multiple medical sensors and retransmits the medical data to the monitor.

The monitor can be coupled with the coupling interface in multiple different ways. However, according to a preferred embodiment of the invention, the monitor is coupled with the coupling interface via an ohmic contact, preferably via an existing conductive facility of a bed, a wheelchair or a walker for the patient. This means that the bed, wheelchair or walker can be provided with a monitor which is contacted via e.g. a metallic device which is an existing part of the bed, wheelchair or walker, respectively.

According to another preferred embodiment of the invention, the monitor is comprised in a handheld device. Preferably the handheld device is a mobile device like a mobile phone. The handheld device can further be provided with the coupling interface making it possible that body-coupled communication with the handheld device is possible by touching or getting close to the human skin.

Further, according to a preferred embodiment of the invention, the coupling interface comprises a conductive plate or sheet which is adapted for body-coupled communication with the medical sensor.

According to another preferred embodiment of the invention, the monitor is coupled with the coupling interface via a wireless connection. Thus, for communication between one or more medical sensors on the one side and the coupling interface on the other side, body-coupled communication is used, making the system secure and efficient, while for the connection of the coupling interface with the monitor a wireless connection, especially a RF connection, is provided. Thus, in case of multiple medical sensors, the coupling interface can act as a gateway, and the wireless connection makes is possible to provide the monitor in a remote place, i.e. in another room or even in another building.

In general, further to the body-coupled communication, no additional communication system for transmitting medical data acquired by the medical sensor is necessary. However, according to a preferred embodiment of the invention, a RF fallback system is provided for RF transmitting the medical data to the monitor in case the body-coupled communication between the medical sensor and the coupling interface breaks down. Such a case might occur, if coupling of the medical sensor to the coupling interface and, thus, to the monitor is achieved by an accordingly equipped bed, and the patient leaves the bed.

Above mentioned object is further addressed by a method for wirelessly monitoring a patient, the method comprising
collecting medical data on the patient's body,
providing a coupling interface for coupling with a monitor,
streaming the collected medical data to the coupling interface via body-coupled communication.

Accordingly, on the protocol side, it is an important idea of the method according to the invention to stream the collected medical data which have to be displayed on a monitor in order to avoid control mechanisms on the transport layer which delay the communication and consume more energy. The reliability of the system is still very high because of the little interference, e.g. no influence on link quality, caused by an external communication system.

This means that the gain of the method according to the invention compared with prior art RF solutions in terms of energy consumption is double: The method itself is much more efficient than any traditional RF communication system and, further, the streaming protocol, which, in general, can be any existing streaming protocol, e.g. RTP or UDP, is optimized for real-time applications and is much more efficient than any traditional transport protocol like TCP or Zigbee.

According to a preferred embodiment of the invention, the data is streamed to the monitor in real-time. Further, it is preferred that a bidirectional body-coupled communication between the medical sensor and the coupling interface is provided. This provides for the possibility that, according to a preferred embodiment of the invention, the medical sensor is requested to start a measurement and to stream medical data via the coupling interface by body-coupled communication. Such a request is preferably performed by the monitor or another mobile device, e.g. a handheld device which is in BCC with the medical sensor.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
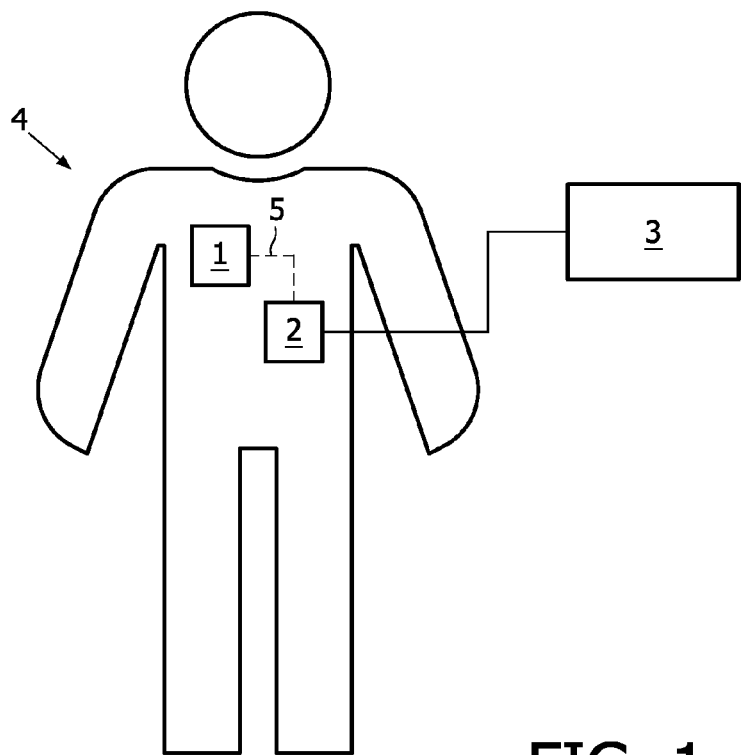
FIG. 1 schematically depicts a system for wirelessly monitoring a patient according to a first preferred embodiment of the invention, FIG. 2 schematically depicts a system for wirelessly monitoring a patient according to a second preferred embodiment of the invention, FIG. 3a, b, c schematically depict a system for wirelessly monitoring a patient according to a third preferred embodiment of the invention, FIG. 4 schematically depicts a system for wirelessly monitoring a patient according to a forth preferred embodiment of the invention, and FIG. 5 schematically depicts a system for wirelessly monitoring a patient according to a first preferred embodiment of the invention.

From FIG. 1, schematically a system for wirelessly monitoring a patient 4 according to a first preferred embodiment of the invention can be seen. This system according to the first preferred embodiment of the invention comprises a medical sensor 1 for collecting medical data and a coupling interface 2 for coupling with a monitor 3, wherein the medical sensor 1 is attached to the patient's 4 body. The medical data collected by the medical sensor 1 is transmitted to the coupling interface via body-coupled communication 5. According to the first preferred embodiment of the invention, the monitor 3 is coupled with the coupling interface 2 via an electrical connection 6. This electrical connection 6 can be very short which means that the coupling interface 2 can be integrated into the monitor 3. Further, the monitor 3 itself can be adapted for body-coupled communication 5 with the medical sensor 1.

Figure 2:
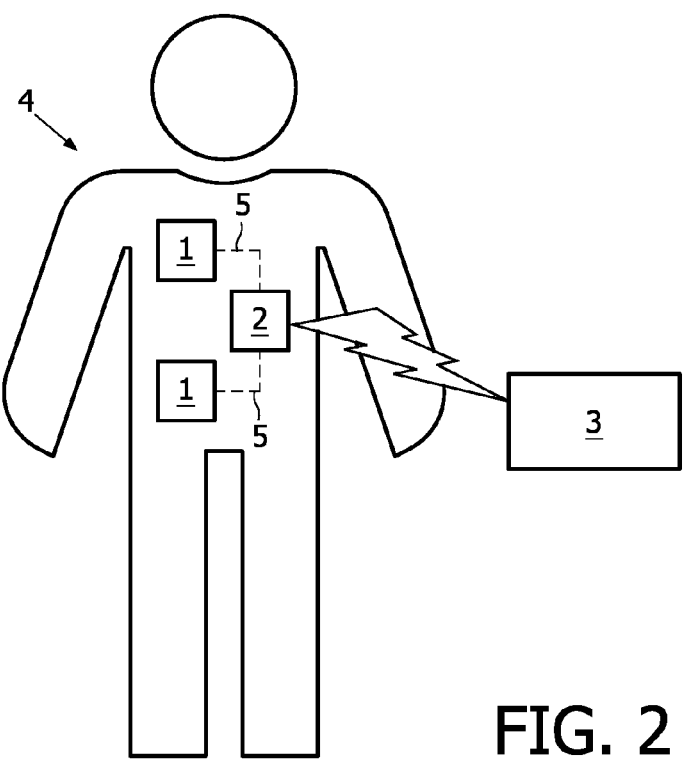

From FIG. 2, schematically a system for wirelessly monitoring a patient 4 according to a second preferred embodiment of the invention can be seen which, in contrast to the system described before, uses a wireless communication between the coupling interface 2 on the one side and the monitor 3 on the other side. Further, according to the second preferred embodiment of the invention, two medical sensors 1 are provided which are attached to the patient's 4 body at different locations and which are adapted for measuring different medical data. Accordingly, in this case, coupling interface 2 acts a gateway for the data acquired by both medical sensors 1 and retransmits this data wirelessly to monitor 3 which can be provided remotely.

Figure 3A:
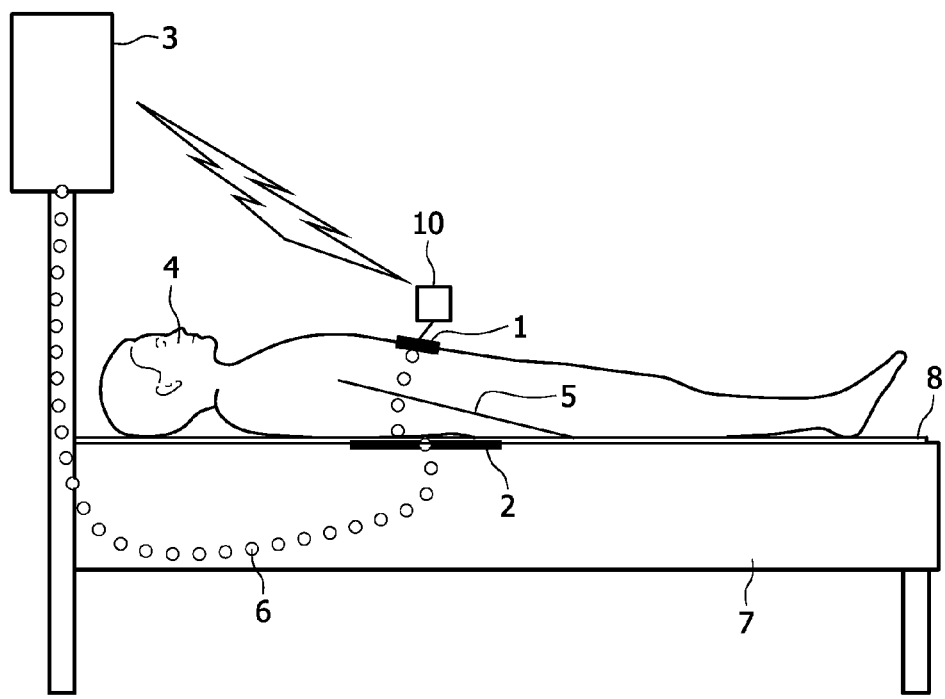
Figure 3B:
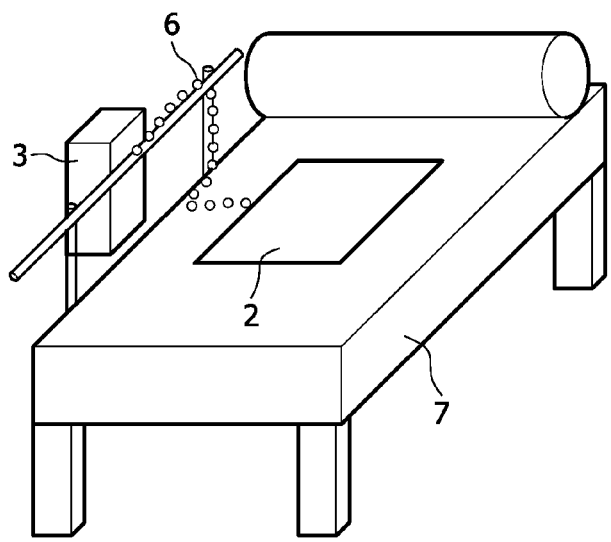
Figure 3C:
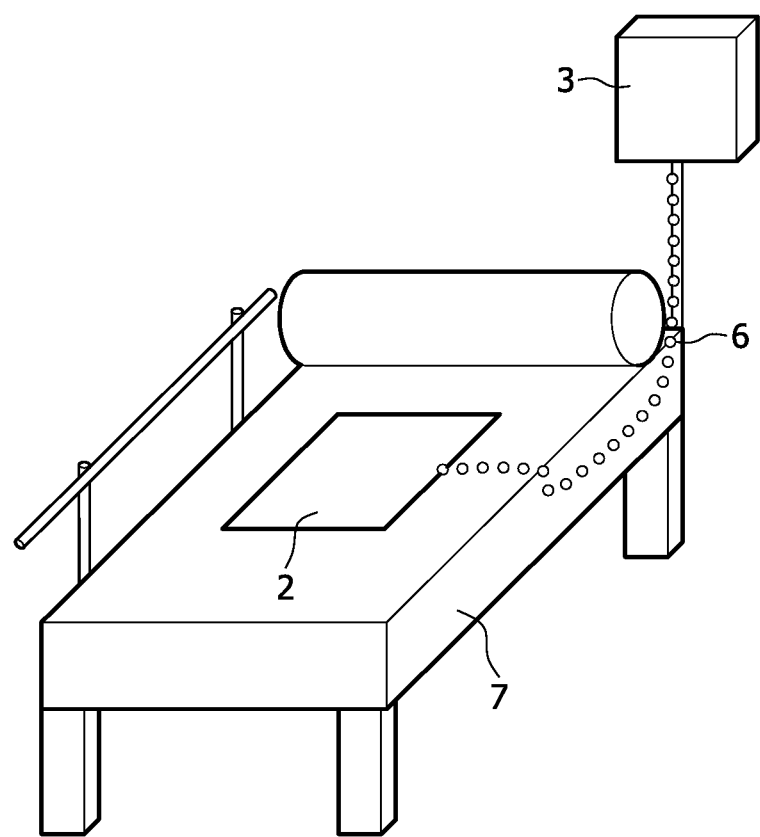

According to the third preferred embodiment of the invention, which can be seen from FIG. 3a, the patient 4 wears a medical sensor 1 which streams data over the body of the patient 4. This data is received by a coupling interface 2 situated on a bed 7. This coupling interface 2 is very thin, approx. 0.1 mm, and is designed with a leaf shape. Therefore it can be easily placed under the sheets 8 of the bed 7. This bed side coupling interface 2 retransmits the data to the monitor 3 which is linked to the bed 7. FIGS. 3b and 3c illustrate two possible configurations for arranging the bed side coupling interface 2 and the monitor 3.

There are two possibilities for linking the bed side coupling interface 2 and the monitor 3 and, thus, enabling BCC data transfer. If, as shown in FIG. 3b, the path between the two devices is conductive enough, e.g. the frame of the bed 7 is made of metal, the data can be simply sent by the bed side coupling interface 2 to the monitor 3 with BCC without any additional devices. However, if the path between the bed side coupling interface 2 and the monitor 3 is not conductive enough, an electrical cable 6 is used to enable BCC data transfer as shown in FIG. 3c.

According to this preferred embodiment of the invention, the medical sensor 1 is constantly streaming data to the monitor 3 as soon as it is turned on. This means that the monitor 3, when it is started, sends a request for data to the medical sensor 1 in order to initiate communication. Of course, this embodiment also applies to a mobile bed, a wheelchair or any kind of walker equipped with a monitor 3 for an ambulating patient. The monitor 3 is attached to the bed 7, wheelchair or walker and, therefore, medical data can always be transmitted as long as the patient 4 lies on the bed 7. If the patient 4 is not in contact with the bed 7 any more, the system according to the third embodiment of the invention is equipped with a RF fallback system 9 which continues to stream medical data as soon as the medical sensor 1 detects an absence of the BCC link.

Figure 4:
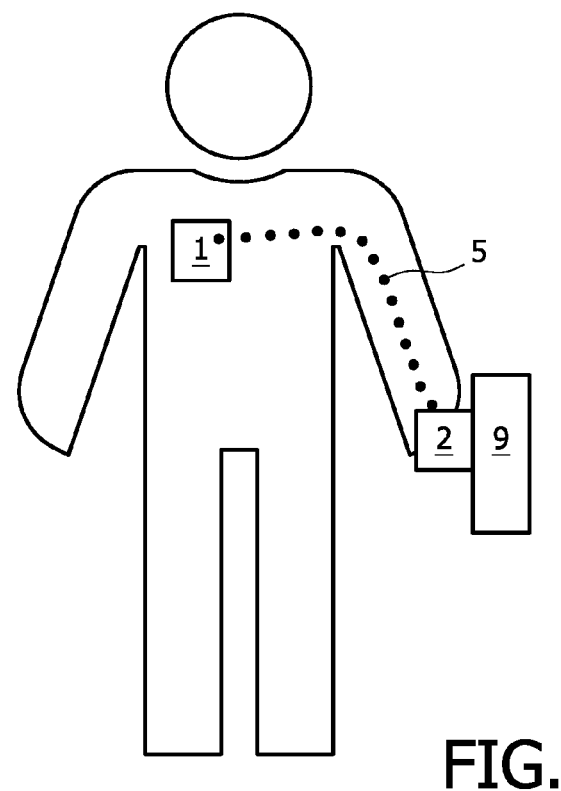

From FIG. 4, a system according to a fourth preferred embodiment of the invention can be seen. While the preferred embodiments of the invention described above are especially suitable for hospital use, this preferred embodiment especially refers to BCC medical data streaming for healthcare at home. The patient 4 wears a medical sensor 1 which streams data over the body of the patient 4. This data is received by a mobile device 9 adapted for body-coupled communication with the medical sensor 1 via the body of the patient 4. The mobile device 9 can be a mobile phone, a PDA, a music player, a portable movie play etc. which is equipped with a screen for displaying the medical data. According to this preferred embodiment of the invention, the medical sensor 1 is the streaming server and delivers the data to the mobile device 9 whereas the mobile device 9 requests information and is the streaming client.

The data exchange between the medical sensor 1 and the mobile device 9 is ruled by the following scheme: The mobile device 9 requests for data when the patient 4 wants to look at his vital signs. The medical sensor 1 acknowledges this request after proceeding to an authentication process and starts the measurements. Then, the medical sensor 1 starts to stream data to the mobile device 9. If the patient 4 does not want to see his data any more, the mobile device 9 sends a request for end of communication. The medical sensor 1 acknowledges this request and stops the measurements in order to save energy.

The medical data is preferably stored in the mobile device 9 and, thus, can be consulted by the patient 4 itself or by a doctor later.

Figure 5:
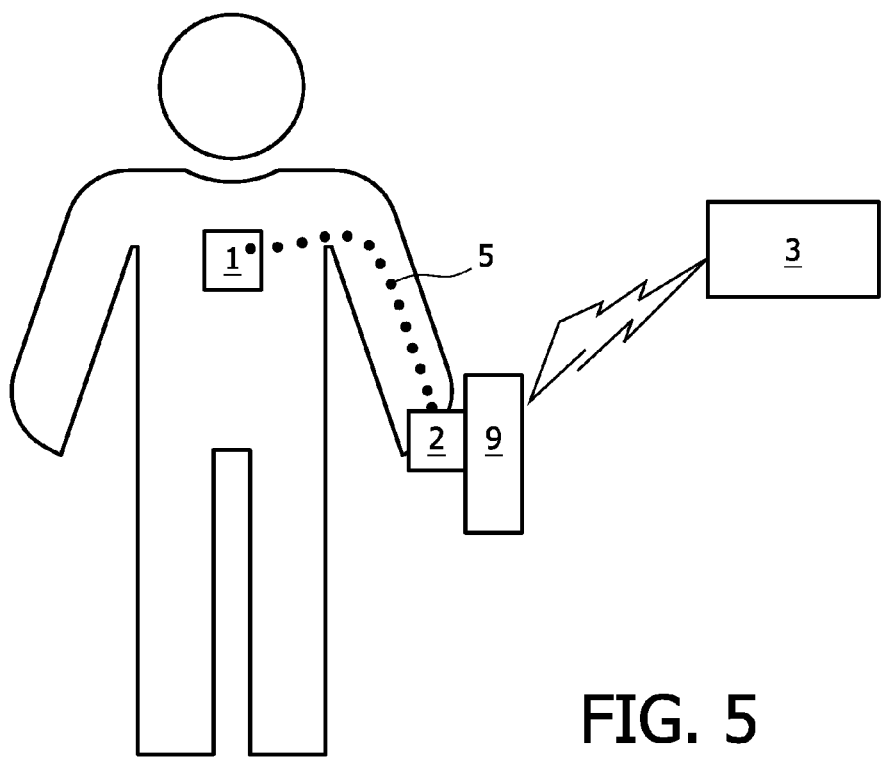

According to a fifth preferred embodiment of the invention which can be seen from FIG. 5, a BCC medical data streaming gateway for healthcare at home is provided. The patient 4 wears a medical sensor 1 which streams data over the body of the patient 4. This data is received by a mobile device 9, e.g. a mobile phone, a PDA with communication capabilities etc., which acts as a gateway between the medical sensor 1 and the monitor 3. It forwards the data received via BCC from the medical sensor 1 to the monitor 3 using a RF protocol like e.g. 802.11/Wifi, 802.15.4/Zigbee, Bluetooth, GSM, UMTS, LTE etc.

According to this preferred embodiment of the invention, the patient 4 can be monitored at home by a doctor who himself is in the hospital. The patient 4 can see the medical data on his mobile device 9, and the doctor can see it on a monitor 3 at the hospital. The data exchange between both devices is ruled by following scheme:

The monitor 3 requests for data to the mobile device 9 when it is started. Then, the mobile device 9 requests for data to the medical sensor 1. The medical sensor 1 acknowledges this request after proceeding to an authentication process and starts the measurements. Then, the medical sensor 1 starts to stream data to the mobile device 9, and the mobile device 9 forwards the data to the monitor 3 in the hospital. If the doctor does not want to see the patient data any more, the monitor 3 sends a request for end of communication to the mobile device 9. The mobile device 9 forwards this request to the medical sensor 1. The medical sensor 1 acknowledges this request and stops the measurements in order to save energy. Finally, the mobile device 9 forwards this acknowledgement to the monitor.

This invention can be applied to the medical domain, especially in a hospital where constant patient monitoring is required. In the case of a large deployment of a wireless patient monitoring solution in a hospital, the costs in terms of battery changes and management can be prominent with prior art RF solutions. The invention does not only provide a more reliable medical data transmission but is also an ultra low power solution for wireless patient monitoring, reducing consequently the costs of the hospital by suppressing heavy management of battery life. Further, this invention can also be applied to healthcare at home where a patient with low risk needs to be constantly monitored but can still stay at home.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A system for wirelessly monitoring a patient, the system comprising:
    at least one medical sensor which collects medical data from the patient and wirelessly streams the medical data over a patient body using body-coupled communication with a streaming protocol including at least one of real time transport protocol (RTP) and user datagram protocol (UDP), the medical sensor including at least one of:
        an electrocardiogram (ECG);
        a photoplethysmograph (PPG);
        a pulse oximetry ($SpO_2$); and
        an electroencephalography (EEG);
    a coupling interface which receives the streamed medical data which is streamed over the patient body via the body-coupled communication; and
    a monitor which receives the streamed medical data from the coupling interface and displays the received streamed medical data.

2. The system according to claim 1, wherein the medical data is collected by multiple medical sensors and the coupling interface acts as a gateway for collecting the medical data streamed from the multiple medical sensors and retransmitting the medical data to the monitor.

3. The system according to claim 1, wherein the monitor is coupled with the coupling interface via an ohmic contact and an existing conductive facility of one of a bed, a wheelchair and a walker.

4. The system according to claim 1, wherein the monitor is coupled with the coupling interface via a wireless connection.

5. The system according to claim 1, wherein the monitor includes a mobile device.

6. The system according to claim 1, wherein
the coupling interface includes a conductive plate or sheet in body-coupled communication with the patient and the at least one medical sensor; and
the monitor receives the streamed medical data via the conductive plate or sheet.

7. The system according to claim 6, further including:
a RF fallback system including an alternative communication path which transmits the streamed medical data from the at least one medical sensor to the monitor when the body-coupled communication between the medical sensor and the conductive plate or sheet of the coupling interface breaks down.

8. A method for wirelessly monitoring a patient, the method comprising:
streaming collected medical data which includes at least one of: electrocardiogram (ECG) data, photoplethysmograph (PPG) data, pulse oximetry ($SpO_2$) data, and electroencephalography (EEG) data over a patient's body to a coupling interface via body-coupled communication using a streaming protocol including at least one of real time transport protocol (RTP) and user datagram protocol (UDP); and displaying the streaming medical data on a monitor which receives the streaming medical data from the coupling interface.

9. The method according to claim 8, wherein the data is further streamed to the monitor in real-time.

10. The method according to claim 8, further including:
establishing a bidirectional body-coupled communication between the medical sensor and the coupling interface.

11. The method according to claim 10, further including:
requesting the medical sensor to start collecting the medical data and stream the medical data via the coupling interface by body-coupled communication.

12. The method according to claim 8, wherein the coupling interface includes a conductive surface disposed under the patient and electrically connected to the monitor and further including:
streaming the collected medical data to the monitor using body-coupled communications between the conductive surface and the patient's body.

13. The method according to claim 8, further including:
streaming the medical data in an alternative communication path which includes RF transmission to the monitor when the body coupled communication is broken.

14. The system according to claim 6, wherein the conductive plate or sheet is connected by a wire with an electrically conductive element of a patient supporting structure.

15. The system according to claim 6, wherein the conductive plate or sheet is disposed on a bed and separated from the patient's body by a sheet.

* * * * *